United States Patent [19]

Schäfer et al.

[11] Patent Number: 5,434,141
[45] Date of Patent: Jul. 18, 1995

[54] MEDICAMENT FOR THE TREATMENT OF HYPERLIPIDAEMIA AND/OR ATHEROSCLEROSIS

[75] Inventors: Hans-Ludwig Schäfer, Erbach-Ernsbach; Werner Schneider, Koblenz, both of Germany

[73] Assignee: Steigerwald Arzneimittelwerk GmbH, Havelstrasse, Germany

[21] Appl. No.: 777,523

[22] PCT Filed: Apr. 6, 1991

[86] PCT No.: PCT/EP91/00654
§ 371 Date: May 21, 1993
§ 102(e) Date: May 21, 1993

[87] PCT Pub. No.: WO91/15214
PCT Pub. Date: Oct. 17, 1991

[30] Foreign Application Priority Data
Apr. 6, 1990 [DE] Germany ............ 40 11 285.3

[51] Int. Cl.⁶ .................. A61K 31/70; A61K 31/725
[52] U.S. Cl. .................................. 514/53; 514/23; 514/824; 536/2
[58] Field of Search ............ 536/2; 514/23, 53, 824

[56] References Cited

U.S. PATENT DOCUMENTS

| 2,370,961 | 3/1945 | Hollander | 536/2 |
| 4,122,179 | 10/1978 | Vegezzi | 536/2 |
| 4,615,891 | 10/1986 | Nocek et al. | 426/231 |
| 4,617,276 | 10/1986 | Nocek | 436/20 |

FOREIGN PATENT DOCUMENTS

| 2103290 | 4/1972 | France . |
| 271415 | 9/1985 | German Dem. Rep. . |
| 54-119038 | 9/1979 | Japan . |
| 59-206045 | 11/1984 | Japan . |

*Primary Examiner*—Ronald W. Griffin
*Attorney, Agent, or Firm*—Nikaido, Marmelstein, Murray & Oram

[57] ABSTRACT

The use of galacturonic acid and derivatives thereof for preparing a medicament for the treatment of hyperlipidaemia and/or atherosclerosis is described.

5 Claims, No Drawings

MEDICAMENT FOR THE TREATMENT OF HYPERLIPIDAEMIA AND/OR ATHEROSCLEROSIS

DESCRIPTION

The invention relates to a medicament which can be administered orally for the treatment and prophylaxis of metabolic disorders, especially to influence lipid and cholesterol metabolism, that is to say hyperlipidaemia and atherosclerosis.

In Western industrialised countries there has for some time been observed to be a rapid increase in metabolic disorders, especially disorders of lipid metabolism, whose main cause is overeating with, at the same time, lack of exercise. There is gradual development of elevated blood levels of particular lipids which increase the risk of atherosclerotic cardiac and peripheral vascular diseases. In this connection, the lipids are transported in the circulation in the form of very small droplets (chylomicrons) which are stabilised by a protein film ($\alpha$- or $\beta$-globulin).

The heavy consumption of meat often results in a surplus of cholesterol because this steroid is already biosynthesised in adequate quantity in the human liver. The natural mechanism of regulation of the cholesterol level is impaired when the diet is rich in lipids, and the result is a permanent elevation of plasma cholesterol. Sparingly soluble cholesterol is deposited, inter alia, in the lining of the aorta, in the cornea and in the lens of the eye. Elevated blood cholesterol levels are at least partly responsible for the development of arterial angioscleroses. Hypercholesterolaemia is a metabolic disorder which always accompanies hyperlipidaemia and which may be very pronounced, for example, in cases of diabetes mellitus.

The clinical pictures, which differ in pathogenesis but have similar symptoms, of hypertriglyceridaemia=-hyperlipidaemia, that is to say the turbidity of the blood serum owing to chylomicrons (droplets which are rich in neutral fats and have a diameter of up to 1 nm) and hypercholesterolaemia, that is to say elevation of the cholesterol content in the blood plasma to above 200 mg are comprised by the collective terms hyperlipoproteinaemia and hyperlipidaemia respectively (compare Pschyrembel, Klin. Wörterbuch).

Used to date for the therapy of hyperlipoproteinaemia are mainly ethyl $\alpha$-(p-chlorophenoxy)isobutyrate, salts of $\alpha$-(p-chlorophenoxy)isobutyric acid and nicotinic acid, and nicotinic acid derivatives, synthetic anion exchanger resins and numerous combination products.

The synthetic anion exchanger resins often lead, because of their chemical and physical properties, to considerable gastrointestinal symptoms. They may, because of their anion-exchanging properties, have an adverse influence on the absorption of other medicaments and of natural minerals.

Plant-based medicaments which can be employed for the treatment of the said metabolic disorders have not hitherto been disclosed. It has now been found, surprisingly, that galacturonic acid has a hypocholesterolaemic action. The experiments described hereinafter demonstrated that intake of galacturonic acid or certain derivatives of this acid results in a distinct lowering of serum cholesterol, that is to say that this compound or compound class is very suitable for the treatment of hyperlipidaemia and atherosclerosis. Thus the invention is, in the first place, directed at the use of galacturonic acid, especially of $\alpha$-D-galacturonic acid of the general formula

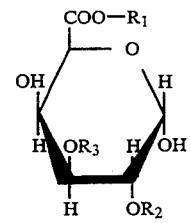

where
$R_1 = H$,
$R_2 = H$ and
$R_3 = H$, for the preparation of a medicament for the prophylaxis and therapy of hyperlipidaemia and/or atherosclerosis.

The invention additionally relates to the use of polymers of galacturonic acid, especially of $\alpha$-D-galacturonic acid of the general formula

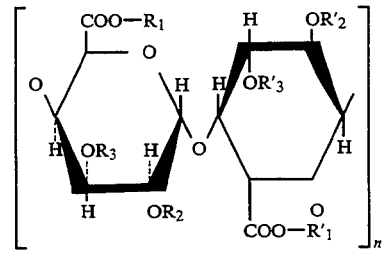

where
$R_1 = H$
$R'_1 = H$
$R_2 = H$
$R'_2 = H$
$R_3 = H$ $R'_3 = H$
n is an integer, for the purpose indicated in claim 1.

The invention also includes the use of methyl esters of galacturonic acid and polymers thereof, especially of $\alpha$-D-galacturonic acid for the purpose indicated in claim 1,
where
$R_1 = CH_3$
$R'_1 = CH_3$ or H,
$R_2 = H$
$R'_2 = H$
$R_3 = H$
$R'_3 = H$.

The scope of the invention also covers the use for the purpose indicated in claim 1 of esters, ethers and/or acetals, containing tertiary or quaternary amine anion exchangers, of galacturonic acid, especially of $\alpha$-D-galacturonic acid and polymers thereof, where in the case of the esters
$R_1 = -CH_2-R_4$
$R'_1 = R_1$ or H
$R_2 = H$
$R'_2 = H$
$R_3 = H$
$R'_3 = H$,
in the case of the ethers
$R_1 = H$ or $CH_3$
$R'_1 = R_1$ $R_2$ or $R_3 = -CH_2-R_4$
$R'_2 = R_2$ or H
$R'_3 = R_3$ or H,
in the case of the acetals

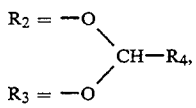

the amine anion exchangers in the general formula are formed by

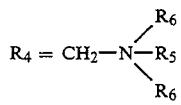

and where in the case of the tertiary amine
$R_5 = H$
and in the case of the quaternary amine
$R_5 = CH_3$ or
$R_5 = [CH_2]_m-CH_3$ or
$R_5 = [CH_2]_m\ CH(OH)-CH_3$
$R_6 = [CH_2]_m-CH_3$, where
m is an integer from 1 to 5.

A particularly preferred embodiment of the invention arises from the use of fermented pectin for the purpose indicated in claim 1. The pectin can also be transformed by fermentation comparatively simply essentially into α-D-galacturonic acid.

Finally, the invention also relates to a medicament which can be administered orally for the treatment of hyperlipidaemia and/or atherosclerosis. It is characterised in that it contains as active substance at least one compound of the composition described in claims 1 5.

In contrast to the purely synthetic medicaments, the abovementioned substances are among the natural constituents of the diet. Galacturonic acid polymers are closely related to pectins which occur in virtually all plant constituents. The compounds can be administered orally as granules, syrup or suspensions.

For the treatment and prevention of pathological processes of biomorphosis, especially of the lipid balance, such as metabolic derangements and vascular changes associated with atherosclerosis, diabetic vascular changes, disturbances of retinal blood flow, on average about 10 to 50 g of the active substance according to the invention are administered each day. They are taken with the main meals.

The experiments reported below demonstrated that α-D-galacturonic acid, the monomer of pectin, shows a hypocholesterolaemic action in the serum. Galacturonic acid is, by contrast with pectin, readily soluble in water and can therefore, as mentioned, be taken without difficulty. It is relatively straightforward to treat cholesterolaemia with α-D-galacturonic acid. No toxic effects are known. α-D-Galacturonic acid is a sugar which occurs very frequently in the plant kingdom. It was possible by acetal-like linkage of the DEAE anion exchanger group to two of the three C—O groups of the pectin monomer galacturonic acid approximately to double the cholesterol-lowering action in the hamster model.

It should also be mentioned that, for example, β-D-galacturonic acid could also be used according to the invention in place of α-D-galacturonic acid. However, the former is considerably more costly, so that as a rule α-D-galacturonic acid will be employed according to the invention.

The experiments reported below demonstrate unambiguously that intake of galacturonic acid results in a significant decrease in the cholesterol and lipid concentrations which are at least partly responsible for the development of hyperlipidaemia and/or atherosclerosis.

The experimental results presented below show that all the substances which contain α-D-galacturonic acid and which were investigated here are effective. Methylation of the acid group of galacturonic acid has only a slight influence on the action of α-D-galacturonic acid. Both the monomer and the polymer of α-D-galacturonicacid have approximately the same efficacy.

Moreover, fermentation of pectin mainly results in galacturonic acid, so that fermented pectin can thus be employed.

However, a further distinct increase in activity occurs on anion exchanger group substitution. This increase is caused by the anion exchanger capacity of the tertiary nitrogen of the DEAE side group. An increase in the action will certainly be achieved also with other anion exchanger groups containing tertiary or quaternary amines.

It is for these reasons evident that all the claimed substances are also effective as hypolipidaemic and antiatherosclerotic medicaments.

Pharmacological tests

Galacturonic acid and derivatives thereof are as a rule well tolerated. The LD 50 of galacturonic acid polymers is far greater than 10 g/kg in rats, hamsters and rabbits. The other abovementioned compounds also display similarly good tolerability. The innocuousness of the compounds is ensured since they are related to or among the natural components of the diet.

Preclinical tests
Experiment 1

3 Groups each of 20 male golden hamsters were fed for 4 weeks with a lipidaemia diet (hamster maintenance diet and 2% cholesterol). The feed in the two treated groups was additionally supplemented with in each case 5% galacturonic acid or DEAE-polygalacturonic acid (DEAE=diethylaminoethyl).

The dose taken was between 4 and 5 g/kg of body weight and day.

After 4 weeks the animals were sacrificed and the serum and hepatic lipid concentration was measured. The results of the analyses are compiled in Tables 1, 2 and 3.

After treatment for four weeks, galacturonic acid significantly ($p \leq 0.05$) lowered the serum concentration of total cholesterol by 20%, of HDL-cholesterol by 20%, of LDL-cholesterol by 23%, of VLDL- and LDL-cholesterol by 20% and of free cholesterol by 19%. In addition, galacturonic acid significantly lowered the serum total lipid concentration by 18% and the phospholipid concentration by 17%. Furthermore, the total lipid concentration in the liver was also significantly reduced by 34%.

After treatment for four weeks, DEAE-polygalacturonic acid significantly lowered the serum concentration of total cholesterol by 43%, of HDL-cholesterol by 47%, of LDL-cholesterol by 46%, of VLDL-cholesterol by 24% and of VLDL- plus LDL-cholesterol by 41% compared with the control animals. In addition, there were also significant reductions of the total lipid concentration by 37% and of the phospholipid concentration by 41% compared with the control animals.

In the animals treated with DEAE-polygalacturonic acid, there were significant reductions in the hepatic cholesterol concentration by 21% and in the hepatic total lipid concentration by 44% compared with the control animals.

Experiment 2

3 Groups each of 20 male golden hamsters were treated for 4 weeks like the animals described in 1. Group 2 were treated with 5% polygalacturonic acid, Group 3 was treated with 5% methyl polygalacturonate in the feed. Group 1 was the lipidaemia control. The serum and hepatic lipid concentrations after the four weeks of treatment are compiled in Tables 4, 5, 6.

After the treatment for four weeks, polygalacturonic acid significantly (p≦0.05 Tables 4 and 5) lowered the serum total cholesterol by 13%, HDL-cholesterol by 15% and free cholesterol by 32%, and the total lipid concentration by 14% and the phospholipid concentration by 19%, compared with the control animals. Furthermore, the treatment with polygalacturonic acid significantly lowered the hepatic cholesterol concentration by 26% and the hepatic total lipid concentration by 25%.

After the treatment for four weeks, methyl polygalacturonate significantly lowered the serum concentration of total (−24%), HDL-(−24%), LDL-(23%), VLDL-(−44%), VLDL-plus LDL-(−22%) and free cholesterol (−41%) (Table 4).

Furthermore, methyl polygalacturonate significantly lowered the serum concentration of total lipids by 18% and of phospholipids by 23% (Table 5). Methyl polygalacturonate significantly lowered the hepatic cholesterol concentration by 29% and total lipid concentration by 32%.

Preparation of Fermented Pectin

A 50 mM $NaH_2PO_4$ buffer pH 4.5, 60° C. and 1 g of pectinase/l (pectinase 5 S, Serra, Aspergillus niger, 0.66 U/mg) is introduced first. Into this solution pectin is stirred stepwise over several hours until the final concentration is about 500 g/l, and 10 g of pectinase per kg of pectin are added. The pH is adjusted to pH 4.5 by adding 5M NaOH.

(continuation Tables 1 to 6)

TABLE 1

Cholesterol concentration in hamster serum after treatment for four weeks (n = 20/group)
Means [mg/dl] ± standard deviation (SD)

|  | Control | Galacturonic acid | DEAE-Poly-galacturonic acid |
|---|---|---|---|
| Total cholesterol | 340 | 271* | 193* |
| SD | ±53 | ±31 | ±40 |
| D |  | −20 | −43 |
| HDL-cholesterol | 148 | 118* | 79* |
| SD | ±23 | ±21 | ±13 |
| D |  | −20 | −47 |
| LDL-cholesterol | 151 | 117* | 82* |
| SD | ±42 | ±24 | ±24 |
| D |  | −23 | −46 |
| VLDL-cholesterol | 42 | 36 | 32* |
| SD | ±10 | ±12 | ±8 |
| D |  | −14 | −24 |
| VLDL + LDL-cholesterol | 192 | 153* | 114* |
| SD | ±47 | ±22 | ±30 |
| D |  | −20 | −41 |
| Free cholesterol | 118 | 96* | 103 |
| SD | ±28 | ±19 | ±20 |

TABLE 1-continued

Cholesterol concentration in hamster serum after treatment for four weeks (n = 20/group)
Means [mg/dl] ± standard deviation (SD)

|  | Control | Galacturonic acid | DEAE-Poly-galacturonic acid |
|---|---|---|---|
| D |  | −19 | −13 |

D = difference in % from the control group
*significance p ≦ 0.05

TABLE 2

Lipid concentration in hamster serum after treatment for four weeks (n = 20/group)
Means [mg/dl] ± standard deviation (SD)

|  | Control | Galacturonic acid | DEAE-Poly-galacturonic acid |
|---|---|---|---|
| Total lipids | 1295 | 1060* | 819* |
| SD | ±177 | ±153 | ±135 |
| D |  | −18 | −37 |
| Phospholipids | 389 | 322* | 228* |
| SD | ±48 | ±40 | ±31 |
| D |  | −17 | −41 |
| Triglycerides | 202 | 216 | 188 |
| SD | ±76 | ±82 | ±55 |
| D |  | +7 | −7 |

TABLE 3

Hepatic lipid concentration (mg/g wet weight) of hamsters after treatment for four weeks (n = 20/group)
Means [mg/dl wet weight] ± standard deviation (SD)

|  | Control | Galacturonic acid | DEAE-Poly-galacturonic acid |
|---|---|---|---|
| Cholesterol | 30 | 27 | 24* |
| SD | ±3 | ±6 | ±8 |
| D |  | −9 | −21 |
| Total lipids | 169 | 111* | 94* |
| SD | ±22 | ±25 | ±33 |
| D |  | −34 | −44 |

D = difference in % from the control group
*significance p ≦ 0.05

TABLE 4

Cholesterol concentration in hamster serum after treatment for four weeks (n = 20/group)
Means [mg/dl] ± standard deviation (SD)

|  | Control | Methyl poly-galacturonate | Polygalacturonic acid |
|---|---|---|---|
| Total cholesterol | 414 | 314* | 361* |
| SD | ±54 | ±44 | ±49 |
| D |  | −24 | −13 |
| HDL-cholesterol | 175 | 133* | 149* |
| SD | ±26 | ±19 | ±23 |
| D |  | −24 | −15 |
| LDL-cholesterol | 199 | 153* | 163 |
| SD | ±63 | ±36 | ±38 |
| D |  | −23 | −18 |
| VLDL-cholesterol | 50 | 28* | 48 |
| SD | ±24 | ±12 | ±16 |
| D |  | −44 | −4 |
| VLDL + LDL-cholesterol | 231 | 181* | 212 |
| SD | ±47 | ±41 | ±42 |
| D |  | −22 | −8 |
| Free cholesterol | 117 | 69* | 80* |
| SD | ±17 | ±10 | ±13 |
| D |  | −41 | −32 |

D = difference in % from the control group
*significance p ≦ 0.05

TABLE 5

Lipid concentration in hamster serum after
treatment for four weeks (n = 20/group)
Means [mg/dl] ± standard deviation (SD)

|  | Control | Methyl polygalacturonate | Polygalacturonic acid |
|---|---|---|---|
| Total lipids | 1563 | 1286* | 1338* |
| SD | ±151 | ±181 | ±201 |
| D |  | −18 | −14 |
| Phospholipids | 474 | 365* | 385* |
| SD | ±52 | ±44 | ±47 |
| D |  | −23 | −19 |
| Triglycerides | 270 | 265 | 269 |
| SD | ±59 | ±80 | ±89 |
| D |  | +2 | — |

TABLE 6

Hepatic lipid concentration (mg/g wet weight) of
hamsters after treatment for four weeks (n = 20/group)
Means [mg/dl wet weight] ± standard deviation (SD)

|  | Control | Methyl polygalacturonate | Polygalacturonic acid |
|---|---|---|---|
| Cholesterol | 30.0 | 21.3* | 22.1* |
| SD | ±3.8 | ±7.3 | ±4.9 |
| D |  | −29 | −26 |
| Total lipids | 89.4 | 60.4* | 67.4* |
| SD | ±11.6 | ±17.4 | ±23.0 |
| D |  | −32 | −25 |

D = difference in % from the control group
*significance p ≦ 0.05

We claim:

1. A method for the prophylaxis of one or more of hyperlipidemia and atherosclerosis which method comprises orally administering to a patient in need of such prophylaxis, a hypocholesterolaemic effective amount of a composition consisting of galacturonide acid of formula I

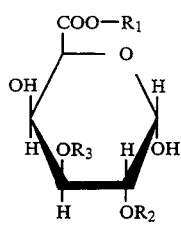

wherein $R_1=H$, $R_2=H$, and $R_3=H$, and a pharmaceutically acceptable carrier.

2. A method for the prophylaxis of one or more of hyperlipidemia and atherosclerosis which method comprises orally administering to a patient in need of such prophylaxis, a hypocholesterolaemic effective amount of a composition consisting of polymers of galacturonic acid of formula II

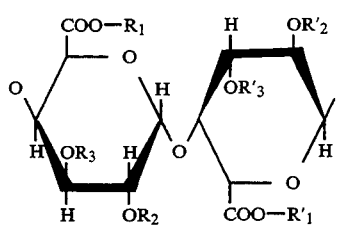

wherein $R_1=H$, $R_2=H$, $R_3=H$, $R'_1=H$, $R'_2=H$, and $R'_3=H$, and n is an integer, and a pharmaceutically acceptable carrier.

3. A method for the prophylaxis of one or more of hyperlipidemia and atherosclerosis which method comprises orally administering to a patient in need of such prophylaxis, a hypocholesterolaemic effective amount of a composition consisting of polymers of galacturonic acid of formula II

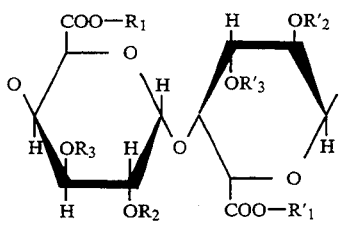

wherein $R_1=CH_3$, $R_2=H$, $R_3=H$, $R'_1=CH_3$ or H, $R'_2=H$, and $R'_3=H$, and n is an integer, and a pharmaceutically acceptable carrier.

4. A method for the prophylaxis of one or more of hyperlipidemia and atherosclerosis which method comprises orally administering to a patient in need of such prophylaxis, a hypocholesterolaemic effective amount of a composition consisting of polymers of galacturonic acid of formula II

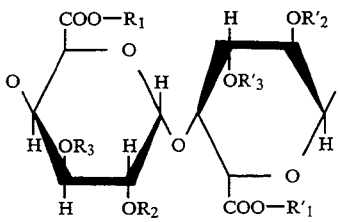

wherein $R_1=-CH_2-R_4$, $R_2=H$, $R_3=H$, $R'_1=R_1$ or H, $R'_2=H$, and $R'_3=H$, or
wherein $R_1=H$ or $CH_3$, $R_2$ or $R_3=-CH_2-R_4$, $R'_1=R_1$, $R'_2=R_2$ or H, and $R'_3=R_3$ or H, or

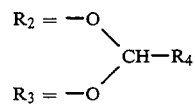

and

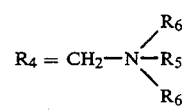

and where in the case of the tertiary amine $R_5=H$ and in the case of the quaternary amine $R_5=CH_3$, $[CH_2]_m CH_3$, or $[CH_2]_m CH(OH)-CH_3$, and $R_6$ is $[CH_2]_m CH_3$, m is an integer from 1 to 5, and n is an integer, and a pharmaceutically acceptable carrier.

5. A method for the prophylaxis of of one or more of hyperlipidemia and atherosclerosis which method comprises orally administering to a patient in need of such prophylaxis, a hypocholesterolaemic effective amount consisting of fermented pectin and a pharmaceutically acceptable carrier.

* * * * *

UNITED STATES PATENT AND TRADEMARK OFFICE
CERTIFICATE OF CORRECTION

PATENT NO. : 5,434,141

DATED : July 18, 1995

INVENTOR(S) : SCHÄFER et al.

It is certified that error appears in the above-identified patent and that said Letters Patent is hereby corrected as shown below:

Column 7, line 35, delete "galacturonide" and substitute therefor --galacturonic--;

around the formula II;

lines 59-67 insert $\left[ \qquad \right]_n$ around the formula II.

UNITED STATES PATENT AND TRADEMARK OFFICE
CERTIFICATE OF CORRECTION

PATENT NO. : 5,434,141
DATED : July 18, 1995
INVENTOR(S) : Schafer et al

It is certified that error appears in the above-indentified patent and that said Letters Patent is hereby corrected as shown below:

Column 8, lines 11-19 insert 

around the formula II.

Signed and Sealed this

Eighteenth Day of June, 1996

Attest:

BRUCE LEHMAN

Attesting Officer     Commissioner of Patents and Trademarks